(12) United States Patent
Ishikawa

(10) Patent No.: US 8,343,203 B2
(45) Date of Patent: Jan. 1, 2013

(54) STEAM-GENERATING WARMING DEVICE

(75) Inventor: Shuji Ishikawa, Tokyo (JP)

(73) Assignee: Kao Corporation, Tokyo (JP)

( * ) Notice: Subject to any disclaimer, the term of this patent is extended or adjusted under 35 U.S.C. 154(b) by 187 days.

(21) Appl. No.: 12/673,349

(22) PCT Filed: Aug. 7, 2008

(86) PCT No.: PCT/JP2008/064228
§ 371 (c)(1),
(2), (4) Date: Mar. 18, 2010

(87) PCT Pub. No.: WO2009/022624
PCT Pub. Date: Feb. 19, 2009

(65) Prior Publication Data
US 2010/0198325 A1 Aug. 5, 2010

(30) Foreign Application Priority Data

Aug. 10, 2007 (JP) .................................. 2007-208697

(51) Int. Cl.
*A61F 7/00* (2006.01)
*A61F 7/02* (2006.01)
*A61F 7/08* (2006.01)

(52) U.S. Cl. .......................... 607/114; 607/109; 424/443

(58) Field of Classification Search .................. 607/109, 607/114; 424/443
See application file for complete search history.

(56) References Cited

U.S. PATENT DOCUMENTS

| | | | | |
|---|---|---|---|---|
| 3,976,049 A * | 8/1976 | Yamashita et al. | ....... | 126/263.02 |
| 4,106,477 A * | 8/1978 | Feld | .......................... | 126/263.05 |
| 5,233,981 A * | 8/1993 | Miyashita | .................... | 607/114 |
| 5,300,104 A * | 4/1994 | Gaudreault et al. | .......... | 607/114 |
| 5,342,412 A * | 8/1994 | Ueki | .............................. | 607/114 |
| 5,366,491 A * | 11/1994 | Ingram et al. | ................. | 607/108 |
| 5,456,704 A * | 10/1995 | Kilcullen | ....................... | 607/111 |
| 5,879,378 A * | 3/1999 | Usui | .............................. | 607/96 |
| 5,984,953 A * | 11/1999 | Sabin et al. | .................... | 607/114 |
| 6,409,746 B1 * | 6/2002 | Igaki et al. | ..................... | 607/109 |
| 6,629,964 B1 * | 10/2003 | Ono et al. | ...................... | 604/304 |

(Continued)

FOREIGN PATENT DOCUMENTS

CN 1491271 A 4/2004

(Continued)

OTHER PUBLICATIONS

Office Action mailed May 8, 2012, in Japanese Patent Application No. 2007-208697 (with English language translation).

*Primary Examiner* — Roy Gibson
*Assistant Examiner* — Kaitlyn Smith
(74) *Attorney, Agent, or Firm* — Oblon, Spivak, McClelland, Maier & Neustadt, L.L.P.

(57) ABSTRACT

A steam-generating warming device includes a holder including a first surface adapted to face the skin of a wearer and an opposite second surface adapted to face outward and a moist heat generating member held in the holder. The moist heat generating member is configured to generate heat as a result of oxidation of an oxidizable metal, generate steam by making use of the heat, and release the steam through the first surface. The steam-generating warming device further includes a water-impregnated, water-retaining sheet adjoining the moist heating member. The water-retaining sheet is preferably disposed between the moist heat generating member and the second surface.

9 Claims, 4 Drawing Sheets

U.S. PATENT DOCUMENTS

| | | | |
|---|---|---|---|
| 6,823,860 B2* | 11/2004 | Igaki et al. | 126/263.05 |
| 6,824,557 B2* | 11/2004 | Tone et al. | 607/114 |
| 6,974,470 B2* | 12/2005 | Tsunakawa et al. | 607/109 |
| 2002/0121624 A1 | 9/2002 | Usui | |
| 2004/0098072 A1* | 5/2004 | Tone et al. | 607/96 |
| 2005/0145250 A1* | 7/2005 | Miyazawa et al. | 128/205.25 |
| 2007/0110790 A1* | 5/2007 | Igaki et al. | 424/443 |
| 2009/0062890 A1* | 3/2009 | Ugajin et al. | 607/104 |
| 2009/0287280 A1* | 11/2009 | Wong et al. | 607/96 |
| 2010/0023099 A1* | 1/2010 | Hidaka et al. | 607/108 |
| 2010/0241199 A1* | 9/2010 | Hidaka et al. | 607/96 |

FOREIGN PATENT DOCUMENTS

| | | |
|---|---|---|
| JP | 8 112303 | 5/1996 |
| JP | 10 108876 | 4/1998 |
| JP | 2002 78728 | 3/2002 |
| JP | 2003 135509 | 5/2003 |
| JP | 2007-319359 | 12/2007 |

* cited by examiner ated at a prescribed tem-
STEAM-GENERATING WARMING DEVICE

TECHNICAL FIELD

The present invention relates to a steam-generating warming device used to apply steam heperature to the skin of a wearer.

BACKGROUND ART

Heat generating devices that have conventionally been used to directly warm the body of a wearer in the cold winter months have come to be used to alleviate various health problems associated with the recent changes in lifestyles, such as lower back pain, shoulder pain, oversensitivity to cold, blurred vision, menstrual cramps, and joint pains. It is predicted that to alleviate or prevent these symptoms through daily life at home will be a popular choice. The recent spread of heat generating devices of easy-to-wear form, such as disposable body warmers, is expected to boost this tendency.

Applicant of the present invention has proposed a steam-generating warming article as a device used to improve a physical function, such as disclosed in patent document 1 (see below). The proposed steam-generating warming article is applied to a body part for the purpose of alleviating or improving a bodily function. In this usage, the shape of the article should be varied depending on the purpose and the body part, and the heat generation temperature and the amount of steam generation should be decided according to the shape.
Patent document 1: US 2007/011790A1

DISCLOSURE OF THE INVENTION

The present invention provides a steam-generating warming device including a holder having a first surface adapted to face the skin of a wearer and a second surface adapted to face outward and a moist heat generating member held in the holder. The moist heat generating member is designed to generate steam by making use of the heat accompanying the oxidation of an oxidizable metal and release the steam through the first surface of the holder. The steam-generating warming device further includes a water-impregnated, water-retaining sheet that adjoins the moist heat generating member.

DETAILED DESCRIPTION OF THE INVENTION

Figure 1:
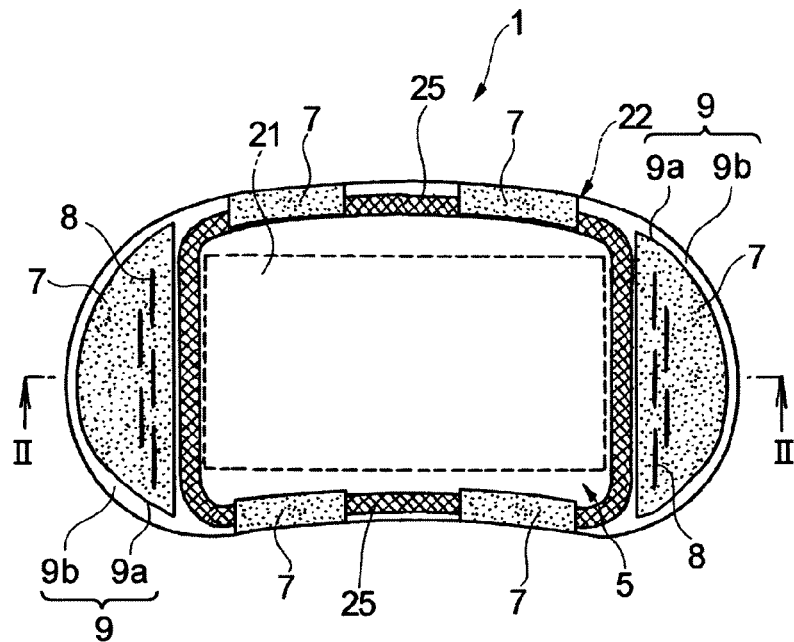
FIG. 1 is a plan of a steam generating pad as a preferred embodiment of the steam-generating warming device of the invention.
Figure 2:
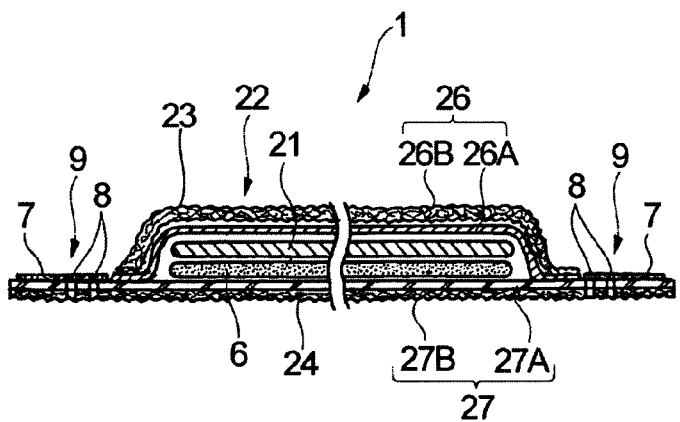
FIG. 2 is a cross-section taken along line II-II of FIG. 1.
Figure 3:
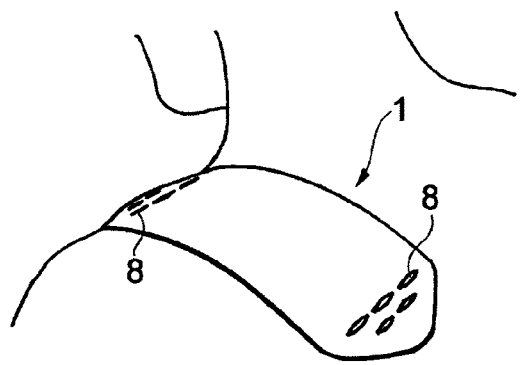
FIG. 3 illustrates a usage of the steam generating pad shown in FIG. 1.
Figure 4:
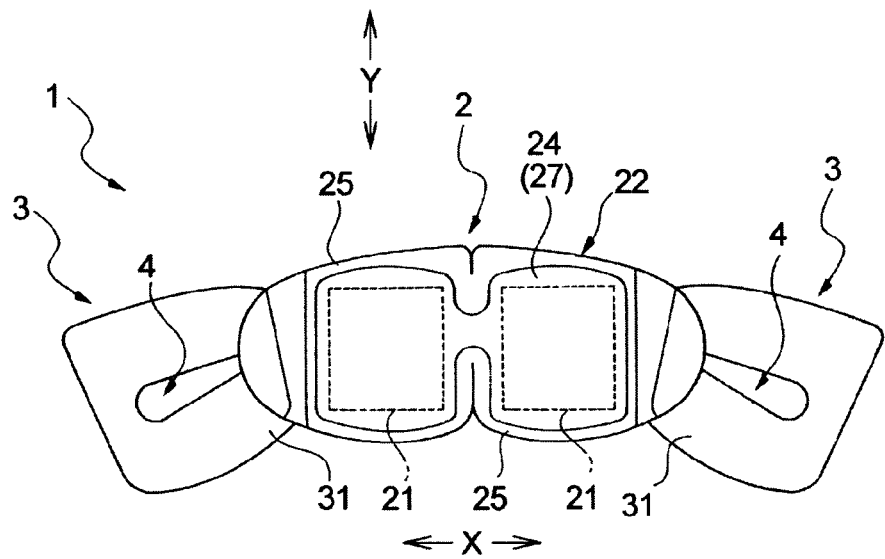
FIG. 4 is a plan of a steam generating pad for eye care as another embodiment of the steam-generating warming device of the invention, with ear loops open.

The invention will be described based on its preferred embodiments with reference to the accompanying drawings. FIGS. 1 and 2 illustrate a steam generating pad 1 as an embodiment of the steam-generating warming device of the invention. The steam generating pad 1 is directly applied to a wearer's body part, such as a shoulder, the lower back, the neck, an arm joint, a leg joint, or the abdomen, to provide moist heat to the body part. For example, it may be applied to a user's shoulder as illustrated in FIG. 3. The time of application of the steam generating pad 1 is from several to about 6 hours. As used herein, the phrase "provide moist heat to" means that the steam generating pad 1 is brought into direct contact with the wearer's skin to give heat to the skin and is brought into indirect contact with the wearer's skin through steam permeable material to give heat to the skin. The term "moist heat" as used herein denotes heat accompanied by steam.

The steam generating pad 1 of the present embodiment has a holder 22 and a moist heat generating member 21 held in the holder 22. The holder 22 has a curved oval or kidney bean shape. The holder 22 is made by joining sheets 26 and 27 along a prescribed position to provide a closed flat space in which the moist heat generating member 21 is placed. The holder 22 has a first surface 23 located proximate to the wearer's skin and an opposite, second surface 24 located distal to the wearer's skin. The sheets 26 and 27 define the first surface 23 and the second surface 24, respectively.

The holder 22 is composed of the two sheets 26 and 27 joined by a peripheral joined portion 25 along a prescribed position to provide a space (a holding portion 5). The peripheral joined portion 25 has the shape of a closed loop thereby to form a closed space inside. The closed space serves as the holding portion 5 for holding the moist heat generating member 21. One moist heat generating member 21 is put in the holding portion 5.

The moist heat generating member 21 contains an oxidizable metal. The moist heat generating member 21 generates heat as a result of oxidation reaction of the oxidizable metal on contact with oxygen and generates steam of prescribed elevated temperature by making use of the heat generated. In more detail, the moist heat generating member 21 contains an oxidizable metal, a reaction accelerator, an electrolyte, and water. The moist heat generating member 21 preferably has, for example, the form of heat generating sheet. Such a heat generating sheet is preferably formed of a fibrous sheet containing an oxidizable metal, a reaction accelerator, an electrolyte, water, and a fibrous material. That is, the heat generating sheet is preferably a water-containing fibrous sheet containing an oxidizable metal, a reaction accelerator, a fibrous material, and an electrolyte. The heat generating sheet is particularly preferably a molded sheet containing an oxidizable metal, a reaction accelerator, and a fibrous material and having incorporated therein an aqueous electrolyte solution. The heat generating sheet is exemplified by a sheet formed by a wet papermaking technique, a laminate structure in which heat generating powder is held in between sheets, e.g., of paper, and a fibrous sheet having an oxidizable metal, etc. supported between constituent fibers. Such a heat generating sheet is produced by, for example, the wet papermaking process taught in commonly assigned US2005/0000827A1 (the disclosure of which is incorporated herein by reference) or an extrusion method using a die coater. Using a steam generating pad of sheet form is advantageous in that the heat generating substance is prevented from being localized thereby to evenly provide moist heat to the wearer's skin whatever posture the wearer takes. Furthermore, a heat generating sheet is advantageous over a heat generating powder in terms of high ability to hold an oxidizable metal.

The heat generating member 21 which is a heat generating sheet is preferably a fibrous sheet made out of 60% to 90%, more preferably 70% to 85%, of an oxidizable metal, 5% to 25%, more preferably 8% to 15%, of a reaction accelerator, and 5% to 35%, more preferably 8% to 20%, of a fibrous material, all by weight, having incorporated therein 25 to 80 parts by weight, more preferably 30 to 70 parts by weight, per 100 parts by weight of the fibrous sheet, of a 1% to 15%, more preferably 2% to 10%, by weight aqueous solution of an electrolyte. The materials making the heat generating sheet can be selected from those commonly used in the art. The materials described in US2005/0000827A1 supra are useful as well.

As illustrated in FIG. 2, the holder 22 contains in its space not only the moist heat generating member 21 but a water-retaining sheet 6 that adjoins the moist heat generating member 21. As used herein, the term "adjoin" indicates that the moist heat generating member 21 and the water-retaining sheet 6 are in direct contact with each other without any other member interposed therebetween. The water retaining sheet 6 is disposed between the moist heat generating member 21 and the second surface 24. The water retaining sheet 6 has nearly the same shape of the moist heat generating member 21, which is, however, not critical to the invention. The water retaining sheet 6 may be larger or smaller in size than the moist heat generating member 21. In order to stably bring about the effect of the water retaining sheet 6 (aqueous electrolyte solution buffering effect, hereinafter described), it is advisable that the water retaining sheet 6 be nearly equal to or larger than the moist heat generating member 21 in size.

The water retaining sheet 6 is a sheet impregnated with water, the term "water" including an aqueous electrolyte solution and pure water. On the other hand, the moist heat generating member 21 is impregnated with an aqueous electrolyte solution. Disposing the water retaining sheet 6 impregnated with water, such as an aqueous electrolyte solution or pure water, to adjoin the moist heat generating member 21 provides the following advantage. The moist heat generating member 21 contains an oxidizable metal and generates moist heat making use of the heat of oxidation reaction of the oxidizable metal. In using iron as an oxidizable metal, for instance, a general oxidation reaction is represented by formula (1):

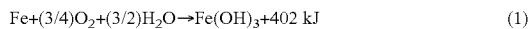

$$Fe+(3/4)O_2+(3/2)H_2O \rightarrow Fe(OH)_3+402 \text{ kJ} \quad (1)$$

Understandably, existence of water is essential for oxidation reaction of the oxidizable metal, and it is required for the moist heat generating member 21 impregnated with an aqueous electrolyte solution to generate heat in a stable manner on contact with oxygen. In some cases, however, the amount of the aqueous electrolyte solution imparted to the oxidizable metal can be non-uniform due to variations of production conditions and the like. For example, in a part where the aqueous electrolyte solution is supplied in excess, the oxidizable metal would be surrounded by the solution and hindered from coming into contact with oxygen, resulting in a delayed rise of heat generation. Conversely, in a part where the aqueous electrolyte solution is in short supply, abnormal or non-uniform heat generation can occur. Such instable heat generation is conspicuous in the case when the distribution of the oxidizable metal in the moist heat generating member 21 is uneven. Hence, the present invention features use of a water retaining sheet 6 impregnated with water in contact with the moist heat generating member 21 so as to supply an adequate amount of an aqueous electrolyte solution to the moist heat generating member 21. A water retaining sheet impregnated with water will hereinafter be referred to as a water-containing, water retaining sheet. Where the moist heat generating member 21 is short of an aqueous electrolyte solution, water is supplied from the water-containing, water retaining sheet 6 to the moist heat generating member 21 to appropriately adjust the aqueous electrolyte solution content in the moist heat generating member 21. Where the moist heat generating member 21 contains too much aqueous electrolyte solution, the excess of the aqueous electrolyte solution is absorbed by the water-containing, water retaining sheet 6 to properly adjust the aqueous electrolyte solution content in the moist heat generating member 21. In this way, the water content around the oxidizable metal is adjusted. In other words, the water-containing, water retaining sheet 6 acts as a buffer for an aqueous electrolyte solution present in the moist heat generating member 21.

The water retaining sheet 6 can be of a flexible sheet material capable of absorbing and retaining water. Examples of the material include fiber sheets, such as paper and non-woven, woven, or knitted fabrics, and porous materials, such as sponge. The fibers of the fiber sheets include those composed mainly of natural fibers, such as plant fibers and animal fibers. Examples of plant fibers include cotton, kapok, wood pulp, non-wood pulp, peanut protein fiber, corn protein fibers, soybean protein fiber, mannan fiber, rubber fiber, hemp, Manila fiber, sisal fiber, New Zealand flax, Luo Buma, coconut, rush, and straw. Examples of animal fibers include wool, goat hair (including mohair and cashmere), alpaca, angora, camel, vicuna, silk, feather, down, small feather, alginate fiber, chitin fiber, and casein fiber. Plant fibers are preferred of them in terms of water absorption and retention. Wood pulp is more preferred. Chemical pulp, such as NBKP or LBKP, is particularly preferred for wood pulp in terms of water absorption and retention and economy.

In the cases where the water retaining sheet 6 is made of paper, the paper may contain the fiber described below for the purpose of enhancing the paper strength within a range that does not impair the water retention. The fiber to be incorporated may be single component fibers of a polyolefin (e.g., high density polyethylene, middle density polyethylene, low density polyethylene, or polypropylene), polyester, polyvinylidene chloride, starch, polyvinyl alcohol, or polyvinyl acetate or a copolymer or a modified product thereof or conjugate fiber of sheath/core configuration having any of the resins recited above as a sheath component. The amount of the fiber to be incorporated is preferably not more than 50% by weight, more preferably 30% by weight or less, even more preferably 10% by weight or less. The water retaining sheet 6 may further contain other components that include, but are not limited to, a fragrance component and a medicinal component. Note that the water retaining sheet 6 does not contain any substance that reacts with water to generate heat, such as an oxidizable metal.

The basis weight of the water retaining sheet 6 preferably ranges from 5 to 125 g/m², more preferably from 15 to 80 g/m², in terms of aqueous electrolyte solution buffering performance that is one of the factors influential on the heat generation characteristics of the moist heat generating member 21. The water-containing, water retaining sheet 6 preferably has a water retention of 10% to 120%, more preferably 30% to 90%, to exert a sufficient aqueous electrolyte solution buffering effect. The water retention (capacity) of a water retaining sheet in terms of amount of an aqueous solution that may be retained by the water retaining sheet as assembled into a steam generating pad is determined according to the following procedure.
(1) Weigh a water retaining sheet 6.
(2) Make a steam generating pad 1 having an aqueous electrolyte solution added. Hermetically put the steam generating pad 1 in a bag made of an aluminum laminate (OPET 12 µm/Al 7 µm/CPP 50 µm) and allow the bag to stand for 12 hours to keep the steam generating pad 1 out of contact with air.
(3) Rapidly remove the water retaining sheet 6 from the steam generating pad 1 and weigh it in a nitrogen atmosphere.
(4) Calculate the water retention in accordance with formula:

Water retention(%)=[{weight of water retaining sheet measured in (3)-weight of water retaining sheet measured in (1)}/weight of water retaining sheet measured in (1)]×100

The weighing of the water retaining sheet 6 in (1) above is carried out in accordance with JIS P8124. The area of the test piece, the number of the test pieces, and the measurement accuracy are adjusted as appropriate to the size of the water retaining sheet 6. The measuring environment is in accordance with JIS P8111.

The inventors' study has revealed that a water retention is correlated with the ratio of the aqueous electrolyte solution to the weight of the moist heat generating member 21. Specifically, there is a positive, linear correlation between the water retention of the water retaining sheet 6 plotted as ordinate and the weight ratio of an aqueous electrolyte solution (the amount of an aqueous electrolyte solution added in the preparation of the moist heat generating member 21) to the moist heat generating member 21 plotted as abscissa. The water retention of the water retaining sheet 6 increases with an increase in ratio of the aqueous electrolyte solution to the weight of the moist heat generating member. Conversely, as the ratio of the aqueous electrolyte solution to the weight of the moist heat generating member 21 decreases, the amount of the aqueous electrolyte solution retained by the water retaining sheet 6 decreases. As a result, even if the amount of the aqueous electrolyte solution added to the moist heat generating member 21 somewhat varies, the variation in amount of the aqueous electrolyte solution actually present in the moist heat generating member 21 is kept small. It is for this reason that the present embodiment of the invention achieves stable heat generation. During heat generation, water moves from the water retaining sheet 6 to the moist heat generating member 21 thereby to realize stable steam generation.

In order to fully appreciate the aqueous electrolyte solution buffering effect, the amount of water infiltrated into the water retaining sheet 6 as assembled in a steam generating pad is preferably 0.5 to 150 g/m², more preferably 4.5 to 72 g/m², while varying with the amount of the aqueous electrolyte solution infiltrated into the moist heat generating member 21. The total amount of water to be infiltrated into the moist heat generating member 21 and the water retaining sheet 6 is preferably 36% to 105%, more preferably 48% to 85%, by weight based on the weight of the oxidizable metal.

Water to be infiltrated into the water retaining sheet 6 may be pure water or an aqueous electrolyte solution. In using pure water, the aqueous electrolyte solution in the moist heat generating member 21 and the pure water in the water retaining sheet 6 come to equilibrium during long time storage of the steam generating pad 1, so that the water retaining sheet 6 comes to contain the aqueous electrolyte solution.

In using an aqueous electrolyte solution as water to be infiltrated into the water retaining sheet 6, the aqueous electrolyte solution to be used may be the same or different from that contained in the moist heat generating member 21. Using the same aqueous electrolyte solution makes it easy to control the oxidation of the oxidizable metal. The concentration of the aqueous electrolyte solution may be the same or different from that impregnating the moist heat generating member 21. In general, satisfactory heat generation performance and steam generation performance are obtained by using an aqueous electrolyte solution having a concentration of 30% by weight or lower, preferably 0.1% to 30%, more preferably 3% to 15%, by weight.

Examples of useful electrolytes include chlorides, sulfates, carbonates, and hydroxides of alkali metals, alkaline earth metals or transition metals. Preferred of them are chlorides of alkali metals, alkaline earth metals, or transition metals for their electrical conductivity, chemical stability, and production economy. Sodium chloride, potassium chloride, calcium chloride, magnesium chloride, iron (I) chloride, and iron (II) chloride are particularly preferred.

At least part of the first surface 23 of the holder 22 has air permeability to allow for passage of air and steam. At least part of the second surface 24 also has air permeability to allow for passage of air and steam. The steam generating pad 1 is used with its first surface 23 facing a wearer's body and the second surface 24 facing outward. The steam generating pad 1 is designed to provide steam generated by the heat generation of the moist heat generating member 21 to the wearer's skin through the first surface 23.

In the present embodiment, the air permeance through the first surface 23 and that through the second surface 24 are properly adjusted so that steam may be released preferentially through the first surface 23. Specifically, the second surface 24 is designed to have an air permeance (JIS P8117) equal to or higher than that of the first surface 23 so that steam may be released through the first surface 23. Instead of being air permeable, the second surface 24 may be air impermeable so as not to allow substantial passage of air and steam.

The term "air permeance" as used herein is a value measured in accordance with JIS P8117 (corresponding to ISO 5636/5-Part 5), which is defined to be the time required for 100 ml of air to pass through an area of 6.45 cm². A higher air permeance means more time needed for air passage, i.e., lower air permeability. Conversely, a lower air permeance means higher air permeability. Air permeance as defined above and air permeability are in a converse relation. In order to allow steam to be released preferentially from the skin side, i.e., the first surface 23, it is preferred that the first surface 23 have equal or higher air permeability than the second surface 24. Proper control of the air permeability of the first surface 23 relative to that of the second surface 24 achieves uniform application of moist heat to the skin.

In the case where the second surface 24 is air permeable, inventors have found that air enters the holder 22 preferentially through the second surface 24 while steam is released preferentially through the first surface 23 when the second surface 24 preferably has an air permeance of at least 100 sec, more preferably 100 to 60,000 sec, even more preferably 1,000 to 60,000 sec, still more preferably 4,000 to 40,000 sec, most preferably 5,000 to 25,000 sec. As a result, air is stably supplied throughout the moist heat generating member 21, allowing the member 21 to generate heat uniformly. Thus, steam generated by the heat generation is uniformly applied to the wearer's skin through the first surface 23. In order for the steam generating pad 1 to maintain a sufficient heat generation temperature for several to about 6 hours, in particular, it is preferred for the second surface to have an air permeance of 50,000 sec or more.

As previously stated, in the case where the outwardly facing second surface 24 is air permeable, the amount of steam released through the first surface 23 and that through the second surface 24 depend on the air permeance of these two surfaces. For instance, there are cases in which although the second surface 24 allows outer air to flow inside, the amount of steam released outside through the second surface 24 is smaller than through the first surface 23. To put it another way, the amount of steam release through the second surface 24 is not large because the amount of air inflow through that side is large. One of the reasons therefor is that both sides of the holder 22 are air permeable. That is, the balance of air permeance between the first surface 23 and the second surface 24 is influential on the amount of air inflow and the amount of steam release through the second surface 24. Hence, when the air permeance of the second surface 24 is equal to or larger to some extent than that of the first surface 23, it is preferred that the air permeance of the second surface 24 be 1 to 3 times that of the first surface 23 in order to suppress steam release through the second surface 24 while securing an air inflow through that side.

In the case when the second surface 24 has a sufficiently larger air permeance than the first surface 23, it is preferred that the air permeance of the second surface 24 be at least 5 times, more preferably 10 or more times, even more preferably 100 or more times, that of the first surface 23. It is otherwise preferred that the ratio of the air permeance of the first surface 23 to that of the second surface 24 be 0.5 or smaller, more preferably 0.2 or smaller. By so controlling the air permeability condition, release of steam from the second surface 24 can be further reduced while further increasing release of steam from the first surface 23.

In the case when the second surface 24 is air impermeable, air supply into the holder 22 and release of steam are exclusively done through the first surface 23.

The air permeance of the first surface 23 is preferably 0.01 to 20,000 sec, more preferably 0.01 to 15,000 sec, even more preferably 0.01 to 10,000 sec, irrespective of whether the second surface 24 is air permeable or impermeable. The most preferred range is from 10,000 to 20,000 sec. It is preferred in the invention that selection of the air permeance of the first surface 23 (the side for steam passage) be followed by decision of the condition of the second surface 24 so as to achieve a desired heat generation temperature and a desired amount of steam generation.

The sheets 26 and 27 providing the first surface 23 and the second surface 24, respectively, may each be a single layer sheet or, as illustrated in FIG. 2, a laminate sheet composed of two or more layers. More specifically, as shown in FIG. 2, in the cases where each of the first surface 23 and the second surface 24 of the holder 22 is formed of a laminate sheet composed of two layers, inner layers 26A and 27A facing inside the holder 22 may be a moisture permeable or impermeable film, and outer layers 26B and 27B facing outward may be of nonwoven fabric. Common nonwoven fabrics may be used, including through-air nonwovens, spun bonded nonwovens, hydroentangled nonwovens, chemically bonded nonwovens, heat bonded nonwovens, and melt blown nonwovens. In a modification of the embodiment illustrated in FIG. 2, moisture permeable films as inner layers 26A and 27A are used to make a holder in which the moist heat generating member 21 and the water retaining sheet 6 are placed, and the holder may be placed in a space formed of nonwoven fabrics as outer layers 26B and 27B. While in the embodiment of FIG. 2 the first surface 23 and the second surface 24 are formed by joining a laminate composed of layers 26A and 26B and a laminate composed of layers 27A and 27B at the peripheral joined portion 25, the layers 26A and 26B and the layers 27A and 27B may not be laminated with each other and, instead, the layers 26A and 27A are joined along their perimeter to make a holder in which the moist heat heating member 21 and the water retaining sheet 6 are placed, and the holder is placed in a space formed by joining the layers 26B and 27B along their peripheral joined portion 25.

As illustrated in FIGS. 1 and 2, the sheet 27 extends outward from the peripheral joined portion 25, which encircles the holding portion 5, in the longitudinal direction of the holder 22 to form a pair of extended portions 9, 9. Each extended portion 9 has a proximal portion 9a that is proximal to the peripheral joined portion 25 and a distal portion 9b that is distal to the peripheral joined portion 25 and contiguous with the proximal portion 9a.

On the skin facing side, i.e., on the surface of the sheet 27A, of the distal portion 9b is provided an attachment member 7. The attachment member 7 is provided outboard the periphery of the holding portion 5 in which the moist heat generating member 21 is held. In FIG. 1, the attachment member 7 is disposed on each of the longitudinal end portions of the holder 22. Each of the attachment members 7 is positioned on the longitudinal centerline of the holder 22. The positions of the attachment members 7 in the holder 22 are the possible most distant from each other. An attachment member 7 is also provided in two positions in each of the upper and lower edges extending in the longitudinal direction. With the attachment members 7 being so arranged, the steam generating pad 1 is stably fixed to the body of a wearer as illustrated in FIG. 3. A pressure-sensitive adhesive may be used to form the attachment members 7. Examples of useful pressure-sensitive adhesives include rubber resins, acrylic resins, and vinyl acetate resins.

The proximal portion 9a of the extended portion 9 is extensible. The proximal portion 9a is extensible in the direction connecting the two attachment members 7, i.e., in the direction of the longitudinal centerline. In the present embodiment, the proximal portion 9a is made extensible by cutting a number of slits 8 therein. Each slit 8 cut in the proximal portion 9a extends in the direction crossing the longitudinal centerline. The slits 8 open wider on pulling the steam generating pad 1 in opposite longitudinal directions, whereby the proximal portions 9a extend in these directions. When the steam generating pad 1 is attached to the body of a wearer, for example, as illustrated in FIG. 3, the proximal portions 9a extend in conformity to the wearer's movement. As a result, an uncomfortable pulling sensation of the skin of the application site can be prevented, and the attachment members 7 are prevented from coming off the skin. In FIG. 1 the slits 8 extend perpendicularly to the longitudinal centerline. While in FIG. 2, the proximal portion 9a of the extended portion 9 is made extensible by cutting the slits, the whole ears including, in some cases, the attachment members 7 may be formed of a stretchable member.

While in the present embodiment the steam generating pad 1 is fixedly attached to the skin of a wearer via the attachment members 7 made of a pressure sensitive adhesive, the steam generating pad 1 may be put into an attachment belt, which is attached to the wearer's body. A supporter may also be used to attach the steam generating pad 1 to the body. The attachment belt is exemplified by the one disclosed in commonly assigned JP 2006-158945A.

The second embodiment of the invention will be described with reference to FIGS. 4 through 7. The description will generally be confined to the differences from the embodiment hereinabove described. Therefore, the description of the embodiment hereinabove described applies to the second embodiment with the exceptions noted hereafter. Reference numerals in FIGS. 4 to 7 common to FIGS. 1 to 3 represent the same elements.

The present embodiment represents application of the steam-generating warming device of the invention as a steam generating pad for eye care. A steam generating pad for eye care 1 provides heat accompanied by steam to a broad area including eyes and surroundings. As used herein, the term "surroundings (of eyes)" is intended to indicate the outer area of opened lid fissures, including eye sockets and the surroundings of eye sockets.

The steam generating pad for eye care 1 includes a main body 2 that is longer than wide and designed to cover eyes while worn and an opposing pair of ear loops 3, 3 attached to near both longitudinal ends of the main body 2. The main body 2 is generally flat and has the shape and size enough to cover eyes and surroundings.

The main body 2 has a moist heat generating member 21 and a holder 22 containing the moist heat generating member 21. The holder 22 is made by joining sheets 26 and 27 by a peripheral joined portion 25 along a prescribed position. The peripheral joined portion 25 is continuous to form a loop which is constricted in the lateral middle (middle in direction X) of the main body 2 to make a peanut shape. As a result, the space defined by the holder 22 is sectioned into two parts that are continuous to each other via a connecting space 28 (see FIG. 5) at the lateral middle in direction X of the main body 2. One moist heat generating member 21 is put in each of the two parts of the space. Since the two parts connect to each other, air is allowed to flow uniformly between the two moist heat generating members 21 thereby to stabilize heat and steam generation from the moist heat generating members 21. Since the moist heat generating member 21 is absent in the connecting space 28 in the middle, the steam generating pad for eye care 1 is easily folded in two in its lateral direction (direction X) when that is packaged. Furthermore, the absence of the moist heat generating member 21 in the middle allows cutting a slit 29 (see FIG. 5) in the lower part of the connecting space 28 of the main body 2. The slit 29 improves the fit of the main body 2 against the root of nose. The middle portion in the lateral direction (direction X) may be otherwise configured such that the connecting space is closed to make two independent spaces in the holder 22 or that the moist heat generating member for the left eye and that for the right eye may be held in the respective holders which are connected via a separate member to make, for example, the shape of glasses.

The holder 22 contains water retaining sheets 6 in addition to the moist heat generating members 21. Each water retaining sheet 6 is disposed between each moist heat generating member 21 and the second surface 24.

In cases where the holder 22 of the present embodiment is air permeable on both the first and second surfaces thereof, the first surface 23 preferably has an air permeance of 50 to 15,000 sec, more preferably 50 to 10,000 sec, and the second surface preferably has an air permeance of 3,000 to 10,000 sec. With the air permeance of both the first and second surfaces being controlled within the respective ranges recited, a sufficient heat generation temperature is maintained for a duration of several minutes to about 15 minutes.

Figure 5:
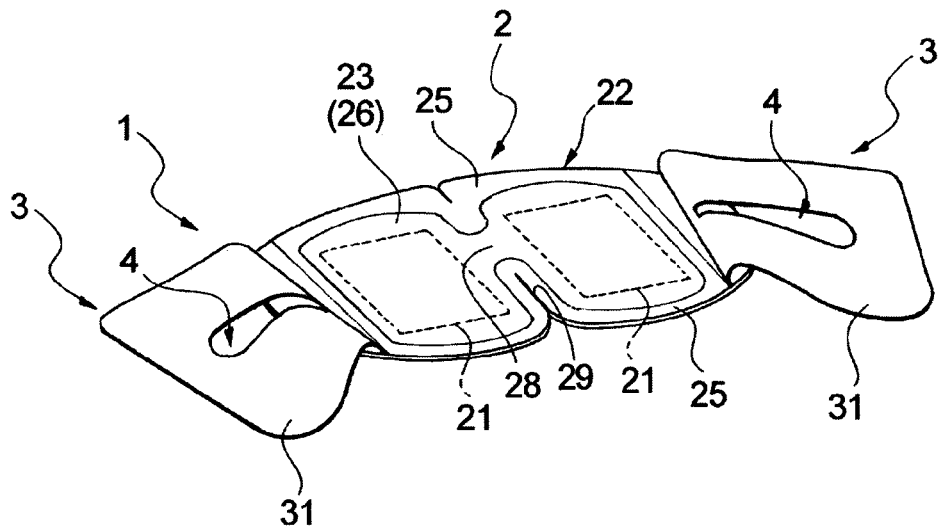
FIG. 5 is a perspective view from the rear side of the steam generating pad with the ear loops open.
Figure 6:
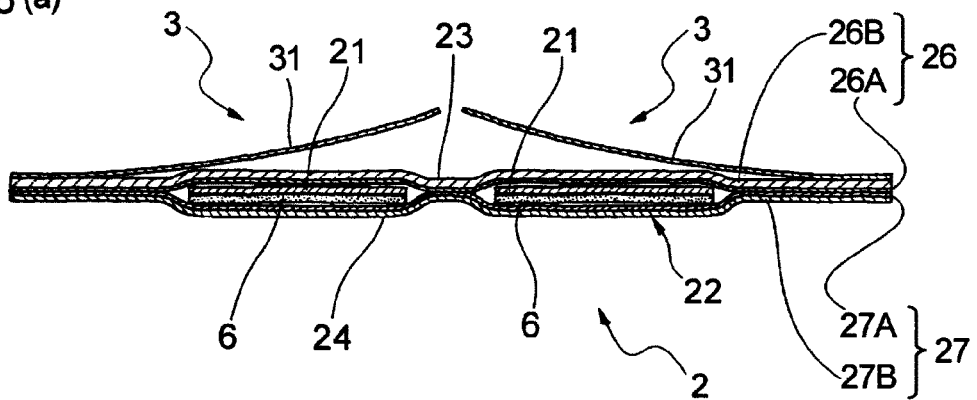
FIG. 6a and FIG. 6b are cross-sections of the steam generating pad for eye care shown in FIG. 4, taken along direction X and Y, respectively, in FIG. 4.
Figure 6:
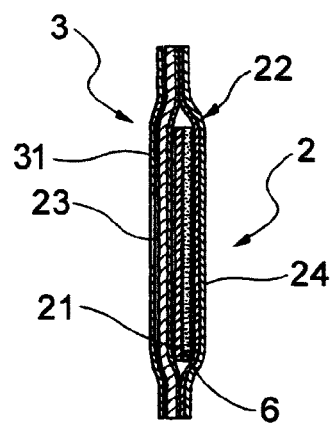

The ear loops 3 are provided on the skin facing side of, and at longitudinal ends of, the holder 22. Each ear loop 3 is formed of a base sheet 31 having an elongated opening 4. The base sheet 31 may be of, e.g., nonwoven fabric, woven fabric, paper, or a resin film. Each ear loop 3 is provided by superposing the base sheet 31 on the skin facing side of the holder 22 and joining the longitudinal end thereof to the holder 22. On use of the steam generating pad for eye care 1, the pair of base sheets 31 are opened outward along the longitudinal direction of the steam generating pad 1 as illustrated in FIG. 5. While the steam generating eye mask of the embodiment shown in FIGS. 4 through 7 has ear loops 3 each formed of a sheet material, the ear loops may be formed of a string attached to the holder.

Figure 7:
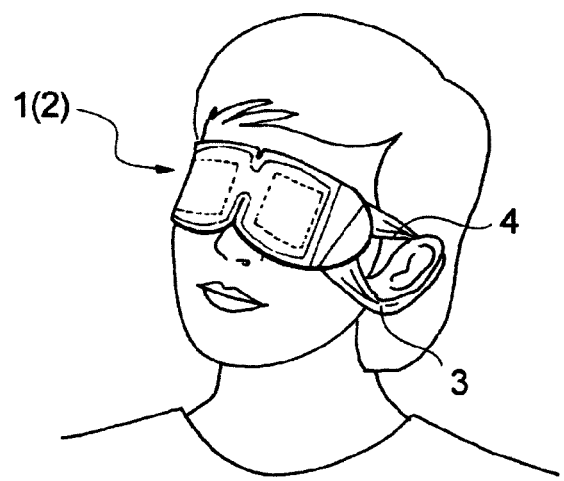
FIG. 7 illustrates the steam generating pad for eye care of FIG. 4 worn by a wearer.

The steam generating pad for eye care 1 of the present embodiment is used with the ear loops 3 looped over the ears of a wearer as illustrated in FIG. 7. The time of use is from several minutes to about 15 minutes. Being so used, the steam generating pad for eye care 1 is able to uniformly apply moist heat from the main body 2 to a wearer whatever posture the wearer takes (e.g., a side lying position or a sitting position). This provides an advantage of improved versatility of the usage of the steam generating pad for eye care 1 having the main body 2. For example, a person may readily wear the eye mask 1 having the main body 2 in his or her lying position at home, or whenever a person feels eye strain at work at the desk, or during train, air or car traveling time.

While the invention has been described with respect to its preferred embodiments, the invention is not limited the embodiments described. For instance, while in the foregoing embodiments the water retaining sheet 6 is interposed between the moist heat generating member 21 and the second sheet 24, it may be disposed between the moist heat generating member 21 and the first surface 23 as long as the steam is sufficiently generated.

Figure 8:
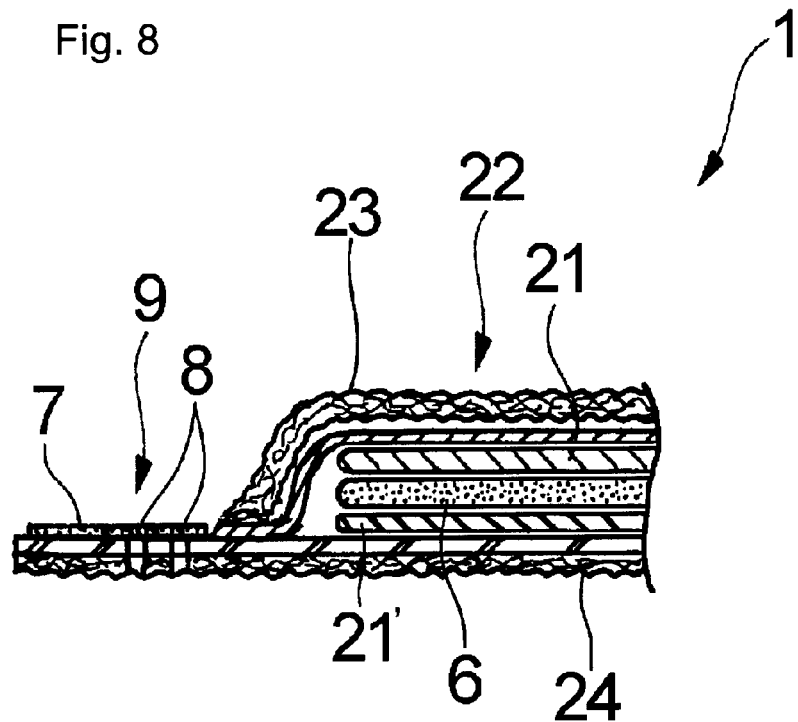
FIG. 8 is a portion of a cross-section taken along line II-II of FIG. 1 according to a further implementation.
Figure 9:
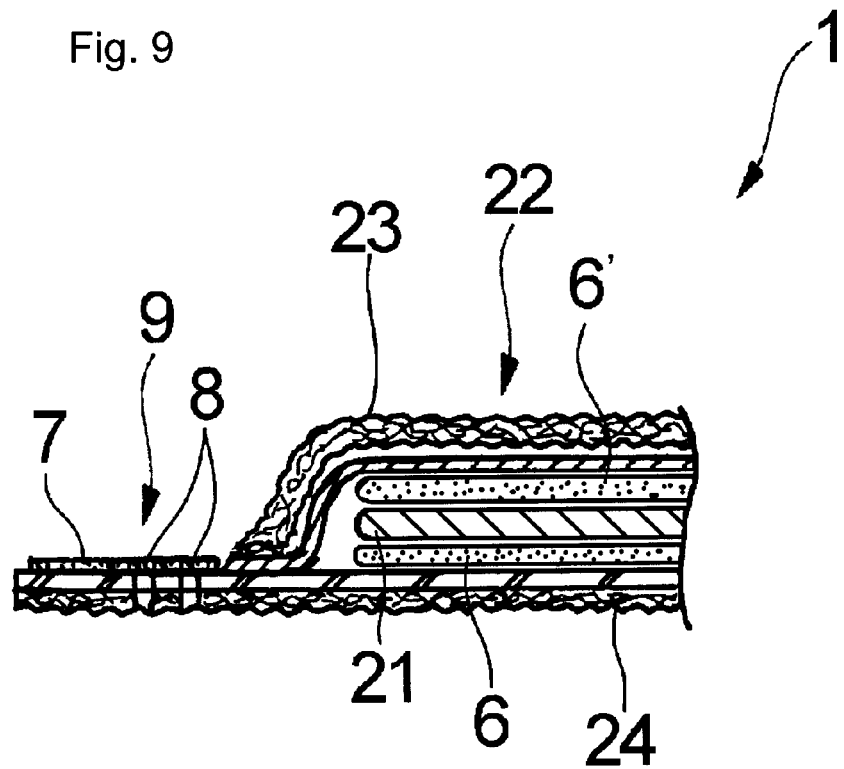
FIG. 9 is a portion of a cross-section taken along line II-II of FIG. 1 according to another further implementation.

For the purpose of further stabilizing heat generation reaction in the moist heat generating member 21, an additional moist heat generating member 21' may be provided between the second surface 24 and the water retaining sheet 6 which is disposed on the second surface 24-facing side of the moist heat generating member 21 las shown in FIG. 8), or an additional water retaining sheet 6' (impregnated with water, e.g., an aqueous electrolyte solution) may be disposed between the moist heat generating member 21 and the first surface 23 in addition to the water retaining sheet 6 between the moist heat generating member 21 and the second surface 24 (as shown in FIG. 9).

EXAMPLE

The present invention will now be illustrated in greater detail with reference to Examples, but it should be understood that the invention is not deemed to be limited thereto. Unless otherwise noted, all the percents and parts are by weight.

Example 1

A steam generating pad shown in FIGS. 1 to 3 was made in accordance with the following procedure.
Composition of Raw Materials:

| | |
|---|---|
| Oxidizable metal: iron powder (RKH (trade name) from Dowa Iron Powder Co., Ltd. | 84% |
| Fibrous material: pulp fiber NBKP (Mackenzie (trade name) from Fletcher Challenge Canada, Ltd.; CSF: adjusted to 200 ml) | 8% |
| Activated carbon (Carboraffin (trade name) from Japan EnviroChemicals, Ltd.; average particle size: 45 μm) | 8% |

To the mixture of raw materials described above were added 0.7 parts of a polyamide-epichlorohydrin resin (WS4020 from Seiko PMC Corp.) as a cationic flocculant and 0.18 parts of sodium carboxymethyl cellulose (HE 1500F from Dai-ichi Kogyo Seiyaku Co., Ltd.) as an anionic flocculant per 100 parts of the solid contents of the mixture (the total of the oxidizable metal, fibrous material, and activated carbon). The mixture was then suspended in industrial water to a solids concentration of 12%.
Papermaking Conditions:

The slurry thus prepared was diluted with water to 0.3% in front of the head box and drained on an inclined short-wire paper machine at a line speed of 15 m/min to form a wet mat.
Drying Conditions:

The wet mat was pressed and dewatered between felt blankets, passed as such between 140° C. heated rollers to be dried to a water content of 5% or less. The dried sheet had a basis weight of 450 g/m² and a thickness of 0.45 mm. As a result of measurement with a thermogravimetric analyzer (TG/DTA 6200 from Seiko Instruments Inc.), the resulting molded sheet was found to be made up of 84% iron, 8% activated carbon, and 8% pulp.
Preparation of Water Retaining Sheet:

Chemical pulp was formed into a water retaining sheet having a basis weight of 35 g/m² by a wet papermaking process. The water retaining sheet had the same size as the heat generating sheet.

Preparation of Heat Generating Sheet:

A hydroentangled PET nonwoven fabric and a porous, moisture-permeable, stretched film of polyethylene containing calcium carbonate were used to form the first surface. The sheets 26A and 26B, as a whole, have an air permeance of 20,000 sec. The second surface was formed of a porous, moisture-permeable, stretched film of polyethylene containing calcium carbonate on the inside and a through-air nonwoven fabric on the outside. The moisture permeable film had a basis weight of 45 g/m2. The through-air nonwoven fabric was made of sheath/core conjugate fiber having polyethylene terephthalate as a core and polyethylene as a sheath and had a basis weight of 20 g/m2. The second surface had an air permeance of 50,000 sec.

A holder having the shape illustrated in FIGS. 1 to 3 was made using these sheet materials. The above prepared molded sheet and water retaining sheet were put and sealed in the holder. The molded sheet and the water retaining sheet were impregnated with 70 parts of a 5% sodium chloride aqueous solution per 100 parts of the molded sheet. The heat generating sheet and the water retaining sheet were put in the holder with the molded sheet on the side of the first surface, while the water retaining sheet on the side of the second surface. There was thus obtained a steam generating pad.

Comparative Example 1

A steam generating pad was obtained in the same manner as in Example 1, except that the water retaining sheet was not used.
Evaluation The steam generating pads obtained in Example 1 and Comparative Example 1 were evaluated in terms of time required for temperature rise up to 40° C. after contact with air (hereinafter referred to as 40° C. rise time) and time during which heat generation at 40° C. lasts (hereinafter referred to as 40° C. duration). The 40° C. rise time and 40° C. duration were measured in accordance with JIS S4100 with the exceptions that the measuring area of the warming device was changed to 180 mm by 180 mm and that the surface temperature of the measuring surface was changed from 30° C. as specified in JIS S4100 to 35° C. The results obtained are shown in Table 1 below.

TABLE 1

|  | Example 1 | Comparative Example 1 |
| --- | --- | --- |
| 40° C. Rise Time | 20 mins | 160 mins |
| 40° C. Duration | 6 hrs | 5 hrs |

Example 2

A steam generating pad for eye care illustrated in FIGS. 4 to 7 was made. A molded sheet and a water retaining sheet were prepared in the same manner as in Example 1. The following procedure was followed for the rest.
Preparation of Steam Generating Pad for Eye Care:

A laminate of spun bonded PET nonwoven fabric, melt blown PP nonwoven fabric, and spun bonded PP/rayon nonwoven fabric was used as sheet 26B of a holder 22. A moisture permeable, porous stretched polyethylene film containing calcium carbonate was used as sheet 26A of the holder. The sheets 26A and 26B as a whole had an air permeance of 9,000 sec. Through-air nonwoven fabric made of sheath/core conjugate fiber having polyethylene terephthalate as a core and polyethylene as a sheath and having a basis weight of 20 g/m² was used as sheet 27B of the holder 22. A moisture permeable, porous stretched polyethylene film containing calcium carbonate (basis weight: 45 g/m²) was used as sheet 27A of the holder. The sheets 27A and 27B as a whole had an air permeance of 8,900 sec. The holder of FIGS. 4 to 7 was made using these sheet materials. The molded sheet and the water retaining sheet were put and sealed in the holder. The molded sheet and the water retaining sheet were impregnated with 39 parts of a 5% sodium chloride aqueous solution per 100 parts of the molded sheet. A ear loop formed of a polypropylene nonwoven fabric was attached to each lateral side of the holder. The heat generating sheet and the water retaining sheet were put in the holder with the molded sheet on the side of the first surface, while the water retaining sheet on the side of the second surface. There was thus obtained a steam generating pad for eye care.

Comparative Example 2

A steam generating pad for eye care was obtained in the same manner as in Example 2, except that the water retaining sheet was not used.
Evaluation The steam generating pads obtained in Example 2 and Comparative Example 2 were evaluated in terms of the highest temperature reached and the time required for reaching the highest temperature after contact with air (hereinafter referred to as time to the highest temperature). The measurements were made in accordance with JIS S4100 with the exceptions that the measuring area of the warming device was changed to 180 mm by 180 mm and that the surface temperature of the measuring surface was changed from 30° C. as specified in JIS S4100 to 35° C. The results obtained are shown in Table 2 below.

TABLE 2

|  | Example 2 | Comparative Example 2 |
| --- | --- | --- |
| Highest Temperature | 53° C. | 48° C. |
| Time to the Highest Temperature | 2 mins | 5 mins |

INDUSTRIAL APPLICABILITY

As described, the steam-generating warming device of the invention has a water-impregnated, water-retaining sheet adjoining a moist heat generating member. The water retaining sheet acts as a buffer for the aqueous electrolyte solution contained in the steam-generating warming device thereby to stabilize heat generation characteristics and, as a result, to stabilize steam generation.

The invention claimed is:

1. A steam-generating warming device comprising:
 a holder having a first surface adapted to face the skin of a wearer and a second surface opposite to the first surface and adapted to face outward;
 a moist heat generating member held in the holder, the moist heat generating member being designed to generate steam by making use of the heat accompanying oxidation of an oxidizable metal and release the steam through the first surface, the moist heat generating member including an aqueous electrolyte solution; and
 a water-retaining sheet arranged adjacent to the moist heat generating member, wherein the water-retaining sheet is impregnated with water, provides an aqueous electrolyte solution buffering effect for the moist heat generating member, and is arranged between the moist heat generating member and the second surface.

2. The steam-generating warming device according to claim 1, further comprising another moist heat generating member arranged between the water retaining sheet and the second surface.

3. The steam-generating warming device according to claim 1, further comprising another water-retaining sheet, which is impregnated with water, arranged between the moist heat generating member and the first surface.

4. The steam-generating warming device according to claim 1, wherein the moist heat generating member is a heat generating sheet comprising an oxidizable metal, a reaction accelerator, a fibrous material, an electrolyte and water, and being adapted to generate heat on contact with air.

5. The steam-generating warming device according to claim 1, wherein the water retaining sheet is a fibrous sheet predominantly comprising plant fiber or animal fiber.

6. The steam-generating warming device according to claim 1, wherein the water-retaining sheet is contained in the space of the holder.

7. The steam-generating warming device according to claim 1, wherein the water-retaining sheet does not contain any substance that reacts with water to generate heat.

8. The steam-generating warming device according to claim 1, wherein the total amount of water to be infiltrated into the moist heat generating member and the water retaining sheet is 48% to 85%, by weight based on a weight of the oxidizable metal.

9. The steam-generating warming device according to claim 1, wherein the moist heat generating member and the water-retaining sheet are in direct contact with each other without any other member interposed therebetween.

* * * * *